United States Patent [19]
Crisio, Jr.

[11] Patent Number: 5,813,855
[45] Date of Patent: Sep. 29, 1998

[54] ILLUMINATED TOOTHBRUSH

[76] Inventor: Raymond A. Crisio, Jr., 4 S. Church St., Belleville, Ill. 62220

[21] Appl. No.: 935,558

[22] Filed: Sep. 23, 1997

[51] Int. Cl.⁶ ..................................................... A61C 1/00
[52] U.S. Cl. ............................................. 433/29; 15/167.1
[58] Field of Search ............................. 433/29; 362/109; 15/167.1

[56] References Cited

U.S. PATENT DOCUMENTS

| | | | |
|---|---|---|---|
| 4,779,173 | 10/1988 | Carr et al. | 362/109 |
| 5,030,090 | 7/1991 | Maeda et al. | 433/29 |
| 5,160,194 | 11/1992 | Feldman | 362/109 |
| 5,306,143 | 4/1994 | Levy | 433/29 |
| 5,658,148 | 8/1997 | Neuberger et al. | 433/29 |

*Primary Examiner*—John J. Wilson
*Attorney, Agent, or Firm*—Robert K. Rhea

[57] ABSTRACT

An illuminated toothbrush is formed by a clear plastic body toothbrush having modified plastic filament bristle tufts in its head portion for admitting light into the bristles from a light source illuminated shaft inserted into a socket in the end of the toothbrush handle opposite the head.

2 Claims, 1 Drawing Sheet

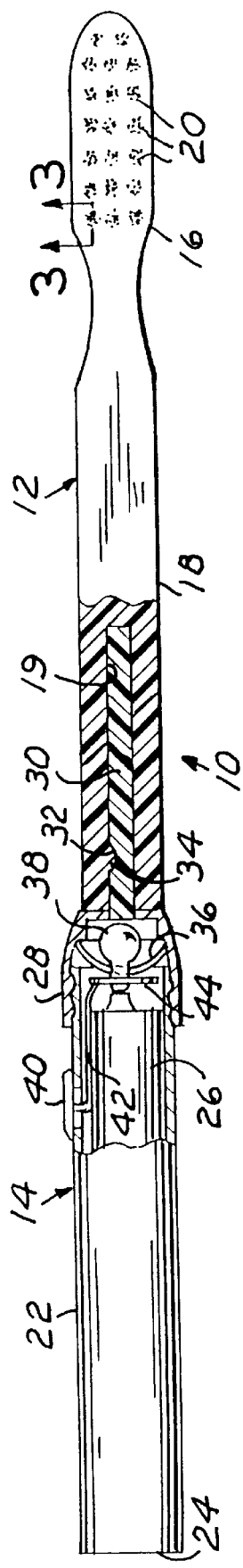
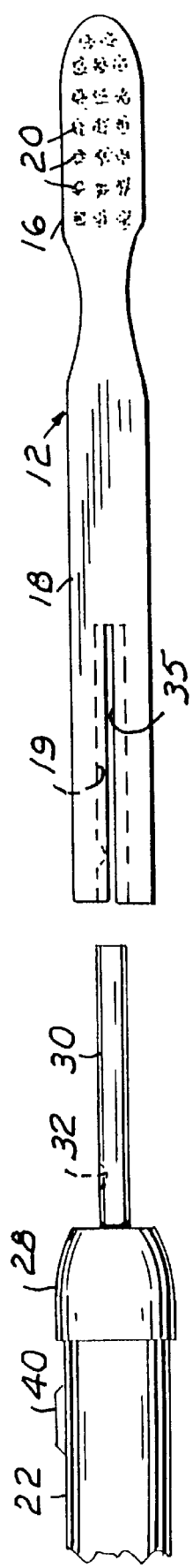
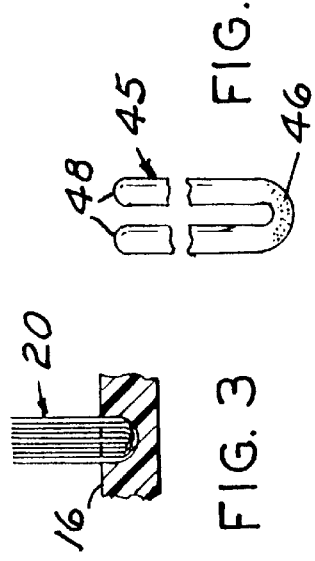

ILLUMINATED TOOTHBRUSH

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

As is well known the best prevention of dental decay and gum disease is a thorough brushing of the teeth following each meal or eating food. Almost everyone in advanced societies has at least one toothbrush. However, tooth decay and gum disease is still prevalent possibly as a result of failure to clean or brush the teeth after eating or improper use of the toothbrush. Since the majority of toothbrushes do not provide light or illumination of the teeth or interior of the mouth while brushing, the user of the toothbrush is not able to see food remaining in the mouth which the toothbrush could remove. Furthermore, children dislike the chore of brushing their teeth.

2. Description of the Prior Art

The Prior Art discloses a number of toothbrushes having optical fibers forming the bristles which are illuminated by light projected against one end of the bristles by a light source in the toothbrush handle. However, this results in a necessary increase in size of the handle and brush head to accommodate the numerous optical fibers. Furthermore, optical fibers have a minimum allowable bend radii resulting in an enlarged bristle supporting head portion of the toothbrush to accommodate the bends of the fibers.

U.S. Pat. No. 4,779,173, issued Oct. 18, 1988 to Carr et al. for Illuminated Brush Device features a toothbrush having optical fibers extending longitudinally through the handle portion of the brush and turned upwardly at the brush head to form the tooth brushing bristles. The handle is axially connected with the bulb end of the flashlight for lighting the ends of the optical fibers adjacent the bulb and transmitting such light to the other ends of the fiber bristles to form an illuminated brush head.

U.S. Pat. No. 5,030,090, issued Jul. 9, 1991 to Maeda et al. for Optical Toothbrush And Method Of Use and U.S. Pat. No. 5,160,194, issued Nov. 3, 1992 to Feldman for Toothbrush With Externally Illuminated Bristles are examples of patents showing the further state-of-the-art.

The Maeda et al. patent illuminating one end of photo-transparent fibers to illuminate the opposite end of the fibers and from a light source to illuminate the interior of a patient's mouth.

The Feldman patent disclosing a flashlight handle having a bulb shining on the exterior of bristles at the head end of a toothbrush.

This invention is believed distinctive over the above named patents by providing a light source which conducts light to the bristle head of a clear plastic toothbrush handle and transfers light to an intermediate portion of the length of the bristles in the tufts embedded in the toothbrush head to illuminate the several ends of the toothbrush bristles.

BRIEF SUMMARY OF THE INVENTION

A source of light such as a flash light has its lens end portion modified to axially support a clear plastic shaft which enters a socket in the handle of a clear plastic toothbrush. Bristles in the head of the toothbrush are formed by nylon filaments having hemispherical end surfaces and doubled back upon themselves and embedded in the toothbrush head with the wall surface of the return end bends of the bristle fibers roughened to break through the exterior seal, as by sandpaper, before insertion into the brush head during conventional manufacture of the toothbrush. Light from the lamp of a source of light passes through the axial shaft, toothbrush handle and enters the bristle filaments to illuminate the ends of the toothbrush bristles.

The principal object of this invention is to provide an illuminated toothbrush axially connected with a source of light in which the bristles of the toothbrush are formed from uniform nylon filaments having hemispherical end surfaces minimizing gum damage when using the toothbrush and in which light enters the bristle filaments medially the ends thereof.

BRIEF DESCRIPTION OF THE SEVERAL VIEWS OF THE DRAWINGS

FIG. 1 is a top view of parts broken away and sectioned for clarity;

FIG. 2 is a fragmentary partially exploded view;

FIG. 3 is vertical cross-sectional view taken substantially along the line 3—3 of FIG. 1; and, FIG. 4 is a greatly enlarged view of one filament of the toothbrush bristles modified intermediate its ends for admitting light into the filament.

DESCRIPTION OF THE PREFERRED EMBODIMENTS

Like characters of reference designate like parts in those figures of the drawings in which they occur.

In the drawings:

The reference numeral 10 indicates an illuminated toothbrush comprising a modified toothbrush body 12 axially connected at one end with a light source, such as a flashlight 14. The toothbrush body 12 is conventional construction formed from clear light ray conducting plastic having a head portion 16 at one end axially integrally connected with a handle portion 18 having a central socket 19 extending inwardly from its end opposite the head 16. The head 16 is provided with a plurality of rows of brush bristle tufts 20, as presently described in more detail.

The flashlight 14 is similarly of substantially conventional construction having a battery case 22 closed at one end 24 and containing a plurality of dry cell batteries 26, only one being shown. The end of the battery case 22 opposite its closed end is closed by a cap 28 axially supporting one end of a clear light ray transmitting plastic rod or shaft means 30 which is cooperatively received by the toothbrush handle socket 19. The shaft wall surface is provided with an indentation 32 cooperatively nesting a lug 34 protruding from the inner wall surface forming the socket 19 to maintain the toothbrush 12 connected with the flashlight 14. The toothbrush handle 18 is longitudinally slit or slotted, as at 35, from its end opposite the head 16 to permit lateral flexing of opposite portions in the socket area for receiving the shaft 30.

The flashlight 14 includes a reflector 36 centrally supporting a bulb 38, disposed adjacent one end of the shaft 30, having its base contacting the battery 26 positive terminal and electrically energized by a switch 40 moving a terminal 42 into contact with an electrical ground 44 for illuminating the bristles of the tufts 20, as presently explained.

The bristle tufts 20 are preferably formed from uniform diameter natural color nylon filaments 45 of selected length having a finish enhancing tuft efficiency, complying with United States Food and Drug Administration regulations, presently marketed by Dupont under the trademark TYNEX. The filaments may be obtained from Dupont, P.O. Box 1217, Parkersburg, W.Va. 26102-1217. A plurality of the filaments 45 form one of the toothbrush tufts 20 and in the manufacture of the toothbrush the filaments 45 are doubled back upon themselves in substantial U-shape (FIG. 4), so that their respective ends are of substantial equal distance from its bight portion 46 and substantially describe a hemispherical surface 48 at the respective ends thereof, highly preferred in the brushing of teeth to minimize damage to gums. Prior to embedding the bristle tufts 20 in the head portion 16, during manufacture of the toothbrush 16 the bight portion 46 of the filaments 45 have the finished "skin" or surface roughened, as by sandpaper or sandblasting, indicated by the dots on the filament bight portions 46 (FIG. 4) which permits light to enter the individual strand or filaments 45 in the respective tufts 20. Light emitted by the lamp is transmitted by the shaft means 30, the clear plastic toothbrush handle 18 and its head 16 and enters the individual filaments 45 of the respective tufts through the bight portions and glows at the end surfaces 48 of the filaments 45.

Obviously the invention is susceptible to changes or alterations without defeating its practicability. Therefore, I do not wish to be confined to the preferred embodiment(s) shown in the drawing(s) and described herein.

I claim:

1. An illuminated toothbrush, comprising;

a toothbrush having a body including a head portion and a handle portion, said handle portion having an axial longitudinally extending socket in its end portion opposite the head portion;

a plurality of rows of toothbrush bristle tufts cooperatively projecting laterally from said head portion, each of said tufts comprising a plurality of plastic filaments of uniform length and diameter and having an exterior surface provided with light ray admitting areas substantially medially the ends thereof, said plastic filaments being doubled back upon themselves and embedded in said head portion;

light producing means including a light bulb and a reflector;

a cap shielding said light bulb;

light conducting shaft means axially connected at one end portion with said cap for receiving light rays from said lamp and disposed at its other end portion within said handle socket; and, energizing means including a source of electrical energy for energizing said bulb, whereby light is transmitted by said shaft means and said toothbrush body into said brush bristles for illuminating the ends of the respective plastic filaments.

2. The toothbrush according to claim 1 in which the energizing means includes:

a case axially connected with said cap;

a battery in said case; and, an electrical circuit including a switch connecting said battery with said light bulb.

* * * * *